US008265958B2

(12) United States Patent
Leonard et al.

(10) Patent No.: US 8,265,958 B2
(45) Date of Patent: Sep. 11, 2012

(54) INTEGRATED ACCESS TO OCCUPATIONAL HEALTHCARE INFORMATION (75) Inventors: Pete Leonard, Wheaton, IL (US); Steve Hlavacek, Elmhurst, IL (US); Kenneth Meeker, Batavia, IL (US); Charles D. Mooney, Ames, IA (US); William Oates, Marion, IA (US); Loren Oury, Wheaton, IL (US); Dennis Picha, Naperville, IL (US); Ilow Roque, San Diego, CA (US); Abhay Pimprikar, Campbell, CA (US)

(73) Assignee: Med-Ebridge, LLC, Wheaton, IL (US)

( * ) Notice: Subject to any disclaimer, the term of this patent is extended or adjusted under 35 U.S.C. 154(b) by 284 days.

(21) Appl. No.: 11/936,612

(22) Filed: Nov. 7, 2007

(65) Prior Publication Data
US 2009/0119149 A1 May 7, 2009

(51) Int. Cl.
*G06Q 50/00* (2006.01)

(52) U.S. Cl. .......................................................... 705/3
(58) Field of Classification Search ......................... 705/3
See application file for complete search history.

(56) References Cited

U.S. PATENT DOCUMENTS

| 5,991,806 | A | | 11/1999 | McHann, Jr. | |
|---|---|---|---|---|---|
| 6,148,297 | A | * | 11/2000 | Swor et al. ........................ | 707/3 |
| 8,086,468 | B2 | * | 12/2011 | Kim .................................. | 705/2 |
| 2005/0256744 | A1 | * | 11/2005 | Rohde et al. ..................... | 705/2 |
| 2007/0244725 | A1 | * | 10/2007 | Sukumar et al. ................. | 705/3 |
| 2008/0071577 | A1 | * | 3/2008 | Highley .......................... | 705/3 |

* cited by examiner

*Primary Examiner* — Thomas Dixon
(74) *Attorney, Agent, or Firm* — Banner & Witcoff, Ltd.

(57) ABSTRACT

Aspects of the present invention provide systems and methods relating to aggregated access to healthcare information. One aspect of the invention relates to providing a single point of access to multiple stakeholders with respect to a medical case that may include information from multiple healthcare providers.

22 Claims, 4 Drawing Sheets

INTEGRATED ACCESS TO OCCUPATIONAL HEALTHCARE INFORMATION

TECHNICAL FIELD

This invention relates to healthcare information access and, more particularly, to systems and methods relating to electronic storage and access to billing and medical records, primarily for Occupational Medicine and Workers' Compensation.

BACKGROUND

Particularly in today's technological computer era, online systems for accessing data have become very popular. As the internet has increased in popularity, more database repositories are being accessed through the internet.

While some systems allow access to healthcare data to certain parties through the internet, they lack a unified point for each of the various stakeholders of a medical case—regardless of whether the stakeholders are a part of the same entity or part of different entities—to gain access to all data, such as doctor's notes and reports, that is relevant to that stakeholder. For example, the most prominent use of electronic data exchange of healthcare data is the use of "clearinghouses" to provide billing information to payors. In these systems, the clearinghouses collect invoices from the healthcare providers and the payors (e.g. insurers, self-insured employers, or third-party administrators) are provided with batch collections of invoices from multiple providers, providing a single access point for some payors, but no case or medical information for the employer or case manager. Some large hospitals or healthcare providers set up systems to exchange invoice data electronically to provide the invoices to the clearinghouses because invoices are usually all that is necessary for General Healthcare. General Healthcare relates to healthcare services other than Occupational Medicine and Workers' Compensation. However, in most Workers' Compensation and Occupational medicine cases, invoices cannot be paid until the doctor's notes and reports have been received. Providers generally use regular postal mail to send the notes to the payor, which leaves out other stakeholders of a medical case and delays receipt of the information to all stakeholders, including the payor, by several weeks.

Currently, many healthcare providers spend substantial financial and personnel resources managing Occupational Medicine cases and processing the large volumes of paperwork. For example, Occupational Medicine and Workers' Compensation cases are a small portion of the medical industry but, in California alone, approximately $400M per year is spent just on scanning and indexing medical case documents received by fax or postal mail.

Thus, there is a need for systems that enable various stakeholders to access relevant Occupational Medicine and Workers' Compensation information, regardless of who the other stakeholders are and regardless of the systems used by healthcare providers. These and other advantages are successfully incorporated in embodiments of the present invention without sacrificing the security that is desired and often required by state or federal regulations for protecting healthcare information.

SUMMARY

Aspects of the invention relate to healthcare information management systems and methods that allow stakeholders to improve communication, streamline processes and better manage costs involved in the management of medical cases. Additional aspects of the invention allow for aggregation of data from numerous and disparate systems without disturbing the documents or processes of the healthcare providers, while delivering the necessary information to the right stakeholders in a timely manner. Aspects of the invention allow stakeholders to manage medical case loads, ensuring that the right information gets to the right team members with ease, while eliminating time and cost inefficiencies that accrue from previous solutions. Still other aspects of the invention allow for any stakeholder of a particular medical case to be a user of the system; a stakeholder's physical location and company or entity affiliation are irrelevant to the stakeholder's ability to use the system.

One aspect of the invention relates to obtaining a copy of information from healthcare providers so that the data can be stored in a uniform manner in a data repository. In one embodiment, a module may be configured to convert data from a format used by the healthcare providers into a common format to standardize the look and feel of the presentation of the information, which enables the data to be formatted for and forwarded to other systems. This may eliminate the need for healthcare providers to invest large amounts of money in installing new technology or systems for mandates such as the senate bill S. 1490 Federal Employees Electronic Personal Health Record Act of 2007, and others like it.

According to another aspect of the invention, the data obtained from the healthcare providers is stored in a manner that keeps the data from one provider separate from the data provided by other providers. Another aspect of the invention relates to providing an interface that is specific to a user of the system based on that user's roles and responsibilities. In one embodiment, the users may access only the information that is relevant to them through a web interface.

Further aspects of the invention relate to providing efficient and effective communication for high-volume, labor- and paper-intensive medical services that require ongoing communication with multiple parties for medical and administrative management of medical cases to provide better outcomes for all involved. In one embodiment, the system manages a workflow such that each user has certain tasks and responsibilities for the medical case. In some embodiments, the system notifies a user of an action required for a particular medical case, at which time the user can access the system to perform the appropriate steps in managing the medical case.

Of course, the systems of the above-referenced embodiments may also include other additional elements, steps, computer-executable instructions, or computer-readable data structures. Additional features and advantages of the invention will be apparent upon reviewing the following detailed description.

DETAILED DESCRIPTION

Aspects of the invention relate to healthcare information management systems and methods and, more particularly, to electronic storage and aggregated access to billing and medical records. Some aspects of the invention allow stakeholders to improve communication, streamline processes and better manage costs involved in the management of medical cases. Additional aspects of the invention allow for a non-invasive aggregation of data from numerous and disparate systems, while delivering the necessary information to the right stakeholders in a timely manner. In an aspect of the invention, a stakeholder of a particular medical case may be a user of the system. In an aspect of the invention, a stakeholder's physical location and company or entity affiliation are irrelevant to the stakeholder's ability to use the system.

One aspect of the invention relates to obtaining a copy of information from healthcare providers so that the data can be stored in a uniform manner in a data repository. In one embodiment, a module may be configured to convert data from any format used by the healthcare providers into a common data format that can be used to standardize the look and feel of the presentation of the information, as well as serve as a known base format from which the data can be converted in order to be understood by other systems. This may eliminate the need for healthcare providers to invest large amounts of money in installing new technology or systems.

According to another aspect of the invention, the data obtained from the healthcare providers is stored in a manner that keeps data for one patient separate from data for another patient and data from one healthcare provider separate from data of another healthcare provider. In one aspect of the invention, data for a patient from one healthcare provider is therefore stored separately from data for the same patient from a second healthcare provider. Another aspect of the invention relates to providing an interface that is specific to a user of the system based on that user's roles and responsibilities. In one embodiment, the users may access the information that is relevant to them through a web interface. The presentation of information may be independent of how the data is stored. Therefore, although some aspects of the invention related to storing the data separately, the separately stored information may be aggregated for viewing.

Further aspects of the invention relate to providing efficient and effective communication for high-volume, labor- and paper-intensive medical services that require ongoing communication with multiple parties for medical and administrative management of medical cases to provide better outcomes for all involved. In one embodiment, the system manages a workflow such that each user has certain tasks and responsibilities for the medical case. In some embodiments, the system notifies a user of an action required for a particular medical case, at which time the user can access the system to perform the appropriate steps in managing the medical case.

The system may be used to aggregate occupational healthcare information. Occupational healthcare may include both Occupational Medicine and Workers' Compensation. In such embodiments, the occupational healthcare information may be separated from non-occupational healthcare data (General Healthcare information)—i.e. only information related to occupational healthcare cases is stored in the system and other information is filtered out by the system.

In certain embodiments of the invention, the system may be partially or wholly implemented with a computer-readable medium, for example, by storing computer-executable instructions or modules, or by utilizing computer-readable data structures.

Figure 1:
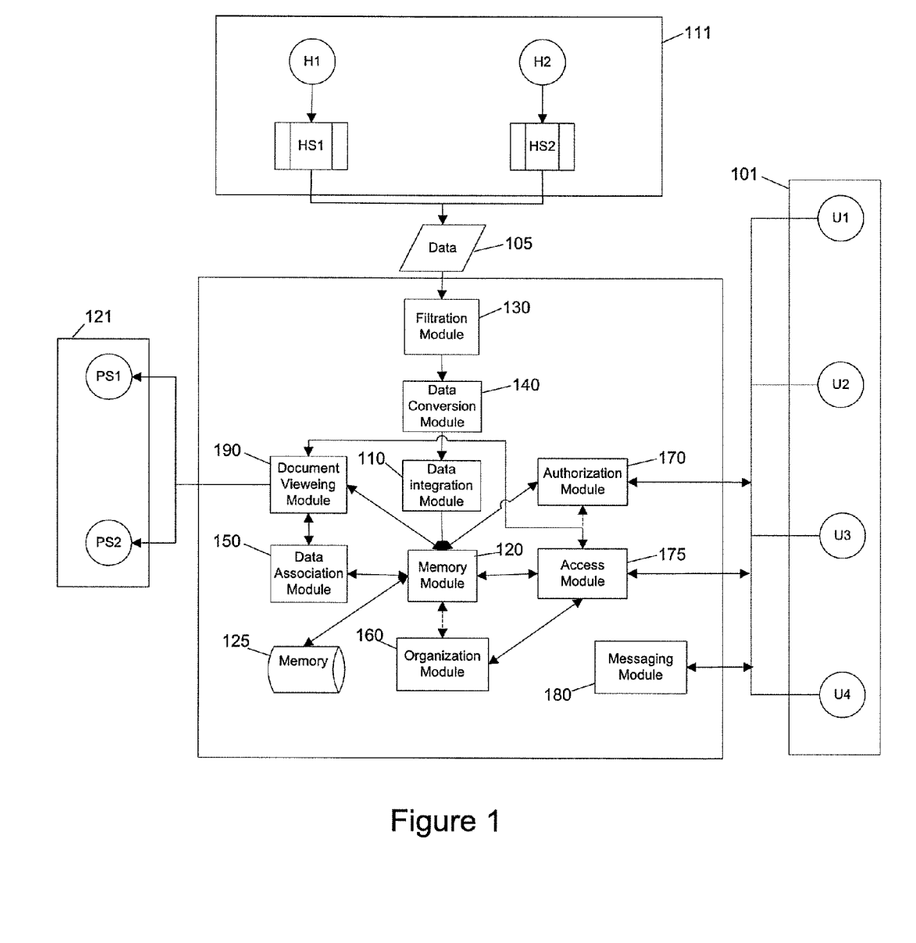
FIG. 1 is a diagram depicting an exemplary set of stakeholders, modules and components according to one embodiment of the invention.

FIG. 1 is a diagram depicting an exemplary set of users, modules and components according to one embodiment of the invention. The exemplary users 101 of the system are identified by U1-U4, the exemplary healthcare providers and systems 111 are identified as provider H1 and provider H2 with systems HS1 and HS2, and potential stakeholders 121 that are view only users of the systems as PS1 and PS2. As one skilled in the art will appreciate, the system may contain various modules and components that may be structured in many ways to allow access of information to users of the system. Moreover, the disclosed systems may comprise more or fewer components or steps, as it is understood the exemplary components and steps illustrate just one embodiment.

Figure 2:
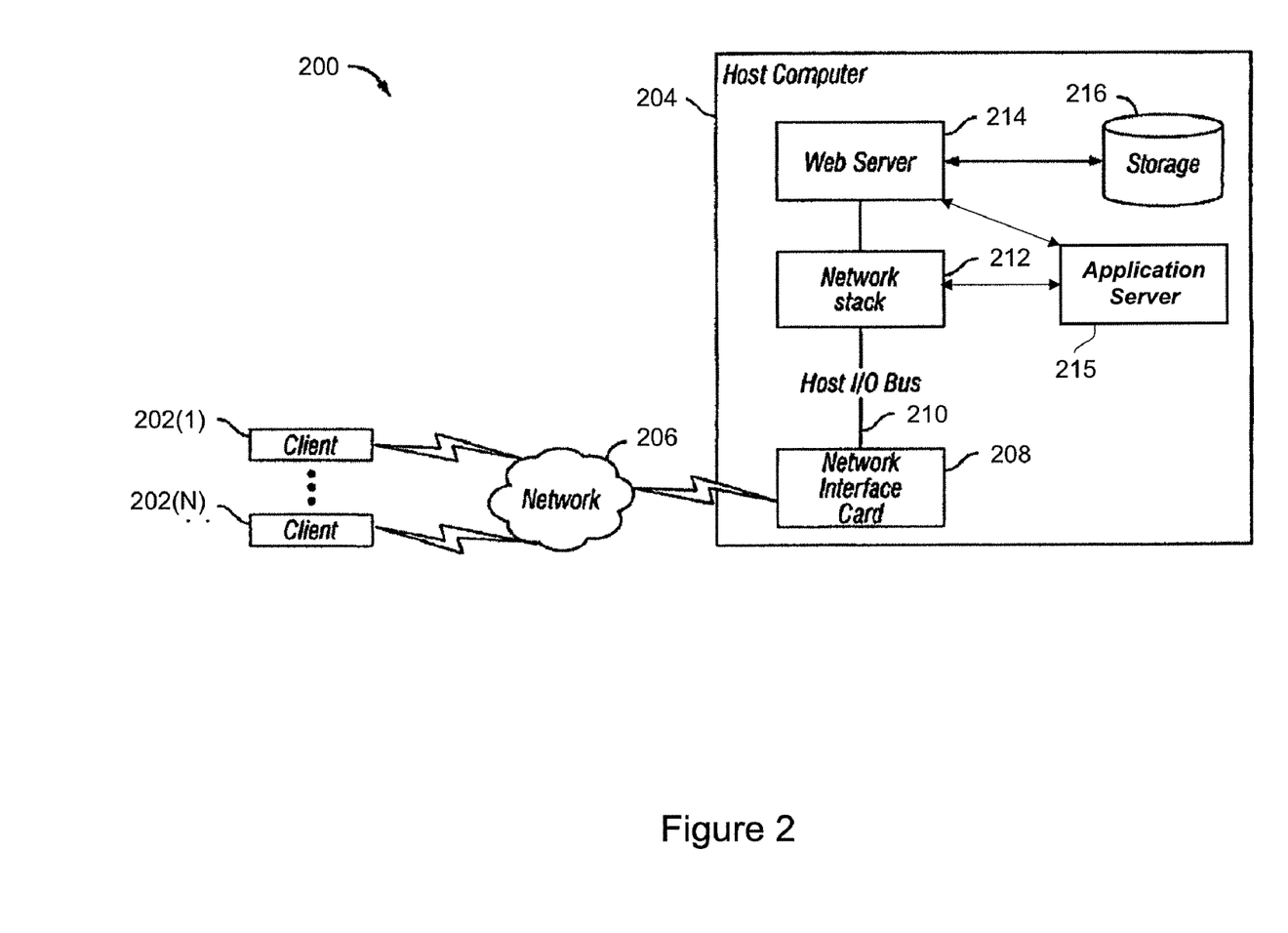
FIG. 2 illustrates one possible network configuration having a client/server network setup that may be used with select embodiments of the invention.

FIG. 2 illustrates an exemplary network configuration 200 in accordance with one embodiment of the invention. As shown in FIG. 2, an embodiment of the invention may allow various users to remotely access and monitor the information that is stored in the memory through a network, such as the World Wide Web. FIG. 2 illustrates one possible network configuration (200) having a client/server network setup. In the network configuration 200, clients 202(1)-202(N) may each request information from a host computer 204 across a network 206. (N represents a whole number.) The client 202 (1), for example, may send a request across the network 206 to access information related to a medical case. In one embodiment, the request may arrive at the host computer 206 at a network interface card (NIC) 208. From the NIC 208, the request may travel along an input/output (I/O) bus 210 and through a network stack 212 to web server 214 running web server software. The web server 214 may also comprise software to allow the system or be electronically connected to a computer-readable medium having the necessary software to allow access to the system.

The web server 214 may handle the request (including any necessary connection setup and information retrievals). The web server 214 may broker the secure connection between the client and the server. The web server 214 may then communicate with an application server 215, which, if necessary, reads information from a local storage mechanism 216 such as a buffer or a data cache. The application server 215 may then return any content requested by the client 202(1) to the client 202(1), with the content traveling through the network stack 212, the I/O bus 210, the NIC 208, and the network 206. Likewise, clients 202(1)-202(N) may each send and receive information through the network 206 to each other, such as for example, secure instant messaging. The client/server configuration may allow users to access the system from anywhere in the world.

In an aspect of the invention, the system may not require that a healthcare provider buy new hardware or purchase or license any software—a simple VPN connection may be all that is needed. In another aspect of the invention, the system does not need to be managed or maintained by the healthcare provider or operated on the premises or at the facilities of the healthcare provider. In yet another aspect of the invention, the system provides a single point of access to information aggregated from multiple systems and healthcare providers, allowing employers, providers, third-party administrators, insurers and others to access medical case information without the need for a significant up-front investment.

Alternatively, in another aspect of the invention, an employer that already tracks occupational healthcare cases using their own "in-house" system does not need to use the web-based user interface of the system to access information aggregated by the system. Instead, through outbound integration from the system to the employer's system, the system may push the data that the employer needs and is authorized to see directly into the employer's system. This is one potential advantage of storing the healthcare information in the system in a non-proprietary data format.

As shown by an exemplary embodiment depicted in FIG. 1, the system may include some combination of a data integration module 110, a memory module 120, a filtration module 130, a data conversion module 140, a data association module 150, an organization module 160, an authorization module 170, an access module 175, a messaging module 180, and a document viewing module 190.

Figure 3:
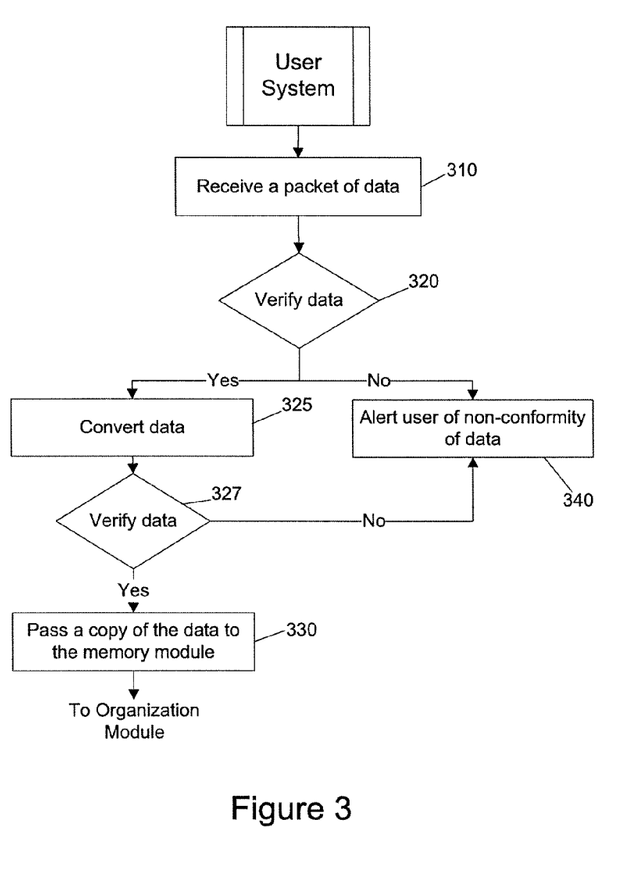
FIG. 3 depicts a flowchart of the method that the data integration module performs on the data it receives from any of the plurality of healthcare providers.

FIG. 3 depicts a flowchart of the method in one aspect of the invention that the data integration module performs on the data it receives from any of the plurality of healthcare providers. In some embodiments, the data integration module receives the data in step 310. The data integration module receives a copy of data 105 from any of a plurality of healthcare providers 111. A healthcare provider 111 can be any of a number of provider types, including doctors, nurses, hospitals, private practices, labs, and clinics. Essentially, a healthcare provider 111 could be any medical professional or entity that adds value to the diagnosis, prognosis, treatment or evaluation of the medical condition of an employee. The data 105 received may be any type of data that a healthcare provider may provide and may be received in any of various formats used by healthcare providers 111. A non-exhaustive list of examples of the type of data 105 that the system might receive include encounter notes, progress notes, letters, work status reports, and invoices.

In an aspect of the invention, the data integration module 110 verifies certain information contained in data 105 in step 320. The verification step 320 may ensure that the necessary information is present to properly store a copy of the data and may allow the data to be organized by medical case, patient, and healthcare provider. In some embodiments, the verification step 320 also ensures that the data contains any required information depending on the type of data that is being stored. In some embodiments, once the data 105 is verified in step 320, then the data integration module 110 passes a copy of the data 105 to a data conversion module 140, which converts the data 105 in step 325. In step 327, after the data 105 is converted in step 325, the data 105 may be verified again to ensure that the data meets further requirements that are discernible once the data 105 is converted. In step 330, the data 105 is passed to the memory module 120. In some embodiments, if the data 105 is not verified, the system, in step 340, alerts the appropriate user of the irregularity or non-conformity of the data. The user is then prompted to correct, add or re-submit the appropriate data, which will then enter the system in step 310 as previously explained.

The memory module 120 may store the data in a memory 125. The memory 125 may be any type of storage such as a database or any other type of data repository as would be understood by one skilled in the art. The memory 125 may be any component, device, or computer-readable medium that is used to maintain information to be accessed at some later time. The memory 125 may also reside in one location or may be spread out over multiple physical and virtual locations.

In some embodiments, the system includes a filtration module 130. The filtration module 130 may filter data received from healthcare providers so that only the desired data is stored in the memory 125 of the system. In one embodiment, the filtration module 130 may be used to exclude all information provided by a healthcare provider that is not related to occupational healthcare. Such an embodiment may be used to create a barrier, separating private data from medical data related to occupational healthcare. The filtration module 130 may be configured to filter data at any point prior to the system allowing access to the data.

In one embodiment, a data conversion module 140 converts the data into a common format such as a non-proprietary data format. One such example would be to convert the data into an extensible markup language, such as XML. Those skilled in the art will realize that other languages or formats may be used. Additionally, the data conversion module 140 may convert the data following a standardized data schema for patient medical information. Such a data schema may be based on guidelines for XML schema provided by a standards developing organization, such as the HL7 XML Schema Guidelines released by Health Level Seven, commonly known as HL7. The data conversion module 140 could convert the data into a common format at any time. FIG. 3 shows the data conversion module 140 converting the data 105 before the data is received by the data integration module 110. In alternative embodiments, the data conversion module 140 could convert the data 105 after the data 105 is received but before the data 105 is verified, after the data 105 is verified but before it is passed to the memory module 120, after the data integration module 110 passes the data 105 to the memory module 120, prior to passing the data 105 to the memory module 120 when the data 105 being sent to a third-party system, or after the memory module 120 receives the data 105 but prior to the memory module 120 sending the data 105 to a third-party system.

In some embodiments of the system, the system may include a data association module 150. The data association module 150 may associate information in the system with a patient and/or with a medical case. This may allow users of the system to easily find all of the information-including medical notes, billing invoices, work status reports, and other data entered into the system—for a particular medical case or for a particular patient.

Referring back to FIG. 1, some embodiments of the system include an authorization module 170. In some embodiments, in order to gain authorization to the system, a user may have to present a digital certificate along with a username and password to the authorization module 170. Once the authorization module 170 grants authorization to a user, the user input may be transmitted through the network, for example as described in relation to FIG. 2, to a computer-readable medium containing the storage, where the copy of the data for a particular medical case may be accessed through an access module 175. The authorization module 170 may grant access to any subset of information in the system, which may include all information.

The use of a tight registration process, including a multi-method security process, helps to control access to all data and authenticate users to the system. In one embodiment, the ability of the system to issue digital certificates along with usernames and passwords may increase security and provides the system with the capability to encrypt and decrypt data. As would be understood by one skilled in the art, there are many methods to ensure security and combining multiple methods increases the security of the system and the data accessed through the system. A few examples of methods and mechanisms of security that may be used in any combination include biometrics, such as fingerprinting, eye scanning, and voice recognition, authentication using a user id and/or password, key cards, and digital certificates.

The system security methods and mechanisms may ensure that the data is secure and that any data access, modification or management is compliant with state or federal standards. For example, in some embodiments, the system may be HIPAA-compliant, providing payors and employers real-time electronic access to medical documents. In other embodiments, the system may provide access that complies with other regulations, such as California state regulations for access to occupational healthcare information.

Embodiments of the system provide benefits through improved efficiency due to the immediate notification that is provided to members of the team when medical notes, invoices, work status reports or other data is received by the system and due to the ability to request and approve appointment requests through the system. Some embodiments of the system also improve efficiency because the stakeholders have one system that allows access to information provided by multiple healthcare providers as opposed to needing to access multiple disparate locations or systems. As explained previously, the system may notify a healthcare provider immediately if certain data is inaccurate or missing. This often improves efficiency because the healthcare provider becomes aware of the incorrect data potentially weeks earlier than they otherwise would through their manual processes.

In some embodiments, the system may include an access module 175 that allows any of the various users 101 to access the data 105 stored in the memory 125 based on a particular user's authorization rights, roles and responsibilities. The access module 175 may provide various ways for the users 101 to access the data stored by the system. In one embodiment, the access module 175 obtains information regarding the access rights of a user from the authorization module 170. For example, in one embodiment, the authorization module 170 may only allow the user to log into the system if the user has an appropriate digital certificate and supplies the correct username and password combination. In this embodiment, the authorization module 170 may provide the access module 175 with information regarding the rights and roles that the user has based on the user's account type and roles associated with that user, as identified by the digital certificate obtained from the user.

The following sections of the specification explain how the access module 175, in conjunction with the organization module 160, may provide access to the data stored in the memory 125. The organization module 160 may generate a logical workflow for the system, which may provide the notifications, reminders and tasks as described below.

In some embodiments, the organization module 160 may provide a logical workflow, which provides the processing steps a document may follow, the notifications and alerts for the document, and the users/roles associated with the processing steps and alerts. The organization module 160 may also organize the information provided by healthcare providers into "injury cases" as opposed to, or in addition to, organizing the information by patient. Organizing the information by injury cases allows for information from various visits and potentially from various healthcare providers related to a specific injury to be logically linked together, such that finding some information related to an injury would allow a user to easily find all other information related to that same injury regardless of the provider of the data. The organization module 160 may use a number of data points to automatically determine whether different treatments belong to one injury case or another because an employee could be receiving treatment for different injuries from the same provider, or a plurality of providers. The organization module 160 may analyze the incoming data and make some determinations based on certain specific data points. The organization module 160 may use a case number if provided by a healthcare provider. However, because the system may receive data from multiple providers, other information may be used to ensure that data 105 is placed into the proper cases, or that the proper new cases are created. Examples of the type of data that may be used to determine whether data 105 is placed in the proper case includes, but is not limited to: the date of injury, the case identification, the visit number, the patient number, the patient's name, the patient's date of birth, and the patient's social security number. Additionally, in some embodiments, the organization module 160 may allow certain roles to organize the documents into cases through the logical workflow and notifications.

The responsibilities of a user of the system help to define the roles that a user will have. The organization module 160 may link authorization, roles, teams, tasks and data with the user. The authorization rights may determine whether a user has any access at all to the system. The roles and teams may define what tasks a user of the system can perform and which cases and/or documents a user of the system can view. The authorization rights (which may include the digital certificate and a username/password combination), a user's role(s), and a user's team(s) function together and may determine what documents that user can see and what actions the user can take within the system.

The system may notify certain users or manipulate certain data based on the status of a particular medical case. For example, when a healthcare provider (such as a diagnosing physician) examines a patient who sustained a workplace injury, the doctor generally must enter notes in accordance with procedures for a particular healthcare provider to track the physician's analysis. This procedure may include entering data electronically into some other system maintained and/or managed at the healthcare provider or may simply be a manual process. The healthcare provider generally must enter billing information as well. When these documents or information are received by the system, the system will notify the relevant stakeholders of the update to the medical case.

In some embodiments, the system includes a system-managed logical workflow for management of medical case information that is received by the system. In some embodiments, the system accepts data from a healthcare provider for a medical case as described with respect to FIG. 3. The data received comprises any combination of medical notes, billing invoices, work status reports, or other information provided by a healthcare provider. After the system verifies the data, the data may be stored in the system. The system may create appropriate notifications for each user role for the particular medical case related to the data received. In other embodiments, a user of the system may request an appointment. The system then creates a notification for each user impacted by the appointment request. Each time a document is added to the system, modified in the system, or replied to through the system, the system may automatically create any notifications necessary for each user who is required to receive or act upon such an addition, modification, or reply.

In one embodiment, the organization module provides notification to an employer when a work status report is received by the system. Such a notification may link directly to the work status report, allowing an employer to understand any potential work restrictions or limitations that may be placed on an employee by a physician. The system also provides employers with immediate access to information regarding work status reports, which allows the employer to reassign the employee to job duties that will not be likely to aggravate an injury or deter rehab efforts. Immediate access also may allow the employer to know when the employee is expected to be able to work and potentially when the employee will be capable of returning to full duties. Immediate notification to the employer may also eliminate a problem with injured employees remaining off the job for longer periods of time than prescribed by a physician due to inefficient data delivery mechanisms between the healthcare provider and the employer.

In another embodiment, the organization module provides notification to an insurer when medical notes and invoices are received by the system. In this embodiment, payment may occur in a timelier manner than in traditional billing methods. In most circumstances, a payor cannot make payment for occupational healthcare cases until both the medical note and the invoice are received by the payor.

There may be various stakeholders that are affected by data being added to the system or appointments requested. The system may provide a single point of access and management of medical case information for teams of users. Each team may comprise a single user or it may comprise multiple users from one or more entities in one or more geographic locations. The system may provide full integration of each team beyond the boundaries of a single enterprise and allows each team to perform the necessary functions with respect to a medical case as a single, cohesive unit.

Figure 5:
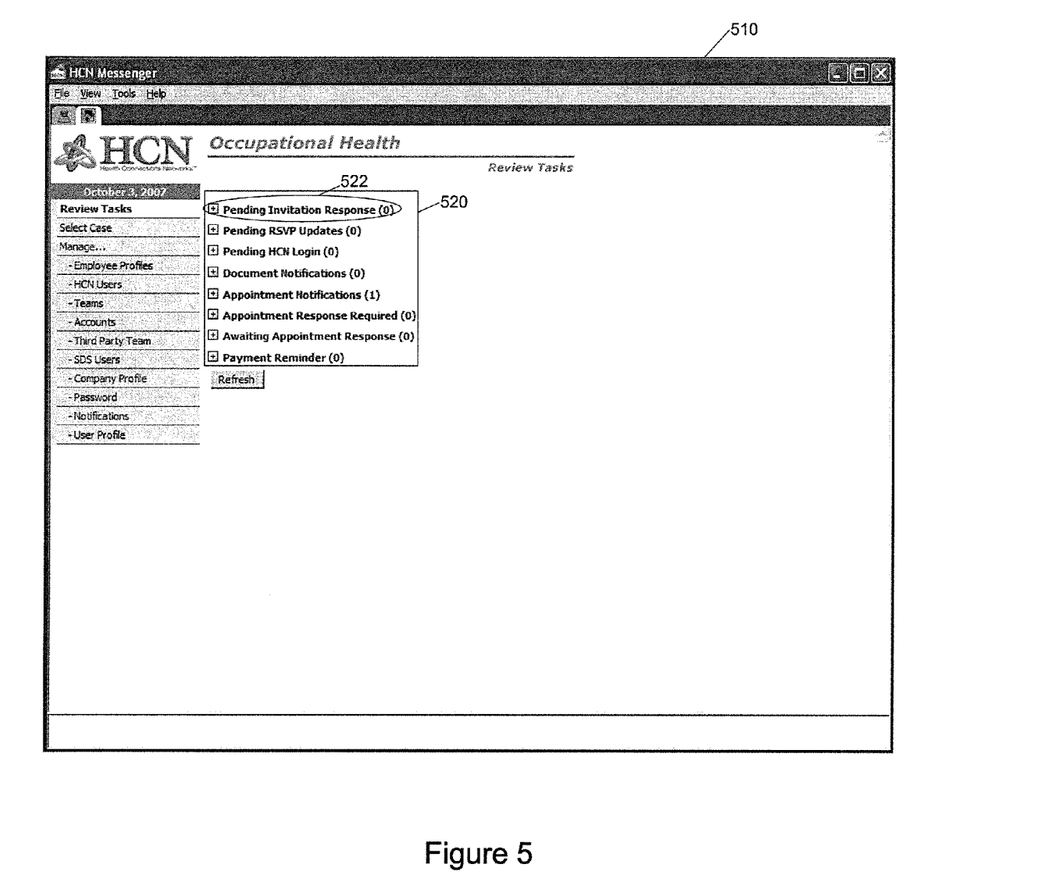
FIG. 5 depicts an exemplary interface comprising a menu of options that the system presents to a user.

Upon accessing the system, an interface may be presented to the user. FIG. 5 depicts an exemplary interface 510 that the system presents in one embodiment of the invention. In some embodiments, the options presented in a menu may vary based on the roles and responsibilities of the user that is being provided options for interfacing with the system. As one skilled in the art would recognize, there are many different ways to present a user with options for navigating the system. For example, in some embodiments, the options may not vary but may simply be inactive options (options that can not be selected) for a user that does not have access to a particular option based on the user's roles and responsibilities. Moreover, other embodiments may present a menu or options in various ways as can be appreciated by one skilled in the art.

Figure 4:
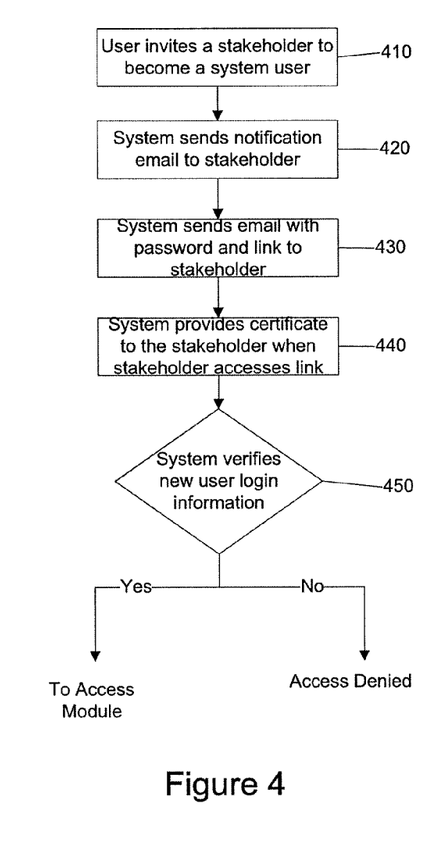
FIG. 4 depicts a flowchart of an exemplary method for a stakeholder to become a user of the system.

FIG. 4 shows the method used in some embodiments for a stakeholder to become a user of the system in accordance with an aspect of the invention. In an exemplary process, if a current user of the system, such as a provider, elects to invite another stakeholder to use the system, the current user, having the appropriate role, may access the system to "invite" another party in step 410. In one embodiment, in step 410, the system accepts information regarding the identification of a stakeholder that may become a new user, including an email address. In response, in step 420, the system may generate an email and send a notification email to the identified stakeholder, notifying the stakeholder that a current user has requested that the stakeholder obtain access to the system. The invited user may verify the identification information input by the inviting user. After verification, in step 430, the system sends another email to the stakeholder providing a temporary password for the system and a link to download a digital certificate. In step 440, in response to the new user accessing the link provided in an email, the system provides a digital certificate to the new user. In step 450, the system accepts login information from the new user, prompts the user to change the temporary password assigned by the system, and the system verifies the data and digital certificate provided by the new user. If the information provided is verified, the system provides access to the system for the new user. In some embodiments, if the information is not verified, the system provides the new user with information as to why access was denied.

Another embodiment of the system that allows a current user to manage and monitor requests to invite additional stakeholders to become users of the system. As explained with respect to FIG. 5, in some embodiments, the system may provide a user with a menu of options and accepts input from the user. As can be seen in FIG. 5, in one embodiment, the menu comprises a list of tasks 520 for the user, one of those tasks including the ability to monitor and manage invitation requests. In some embodiments, when a user has invited another stakeholder to become a user, the system adds an item to a queue indicating that the user has issued an invitation that is still pending 522. If a user clicks on an item indicating a stakeholder invitation that has been issued, the system allows the user to review the information for the invited stakeholder. The user may then optionally use the system to cancel the registration or resend the invitation. If the registration is cancelled, the stakeholder may no longer use the links in the email sent to the stakeholder and the stakeholder's entry will be removed from the queue. If the user elects to resend the invite, the system will send a duplicate email to the stakeholder.

In some embodiments, the system may also provide an option to select a medical case to view and manage the information related to the case. In one embodiment, the system presents an interface for a user to enter information relating to a medical case, such as a patient's name to find the information related to a medical case to which the user has access. Upon selection of a medical case, the system presents documents and information related to that medical case that have been received by the system and to which the user who selected the case has access.

In one embodiment of the invention, the organization module may be further configured to provide reminders to users that have not responded to pending tasks. In some embodiments, the organization module sends an email to a user who has not taken a necessary action on a task. In other embodiments, the organization module creates another notification for the user who has not taken a necessary action on a task. In still other embodiments, the organization module both sends an email and creates a notification for the user who has not taken a necessary action on a task. In this manner, the organization module further improves the efficiency of the handling of occupational healthcare cases by providing reminders to users who are creating delays in the processing or review of information entered into the system.

In one embodiment of the invention, the system may include a messaging module 180. The messaging module 180 may provide secure messaging between users of the system. In an exemplary use of the messaging module 180, a payor may access a medical note and billing invoice. The payor may have a question regarding the billing invoice and may want to contact the healthcare provider that submitted the data. The payor may determine whether the healthcare provider is logged into the system and, if so, attempt to contact the healthcare provider through the messaging module 180. Another exemplary use of the messaging module 180 would be if one healthcare provider notices a second healthcare provider has entered a diagnosis into the system and has questions or comments regarding the medical note entered. Again, the first healthcare provider could contact the second healthcare provider to ask the second healthcare provider clarifying questions.

In one embodiment, the messaging module 180 is an implementation of a commercially available instant messaging tool embedded inside the system. In such an embodiment, the messaging is secure and encrypted. As one skilled in the art would recognize, there are many features of commercially available instant messaging tools that, when incorporated with the features of the present invention could provide important real-time communications within a context of healthcare data and services that could increase efficiencies and reduce the need for corresponding through other, more time-consuming methods.

In some embodiments, the system may include an asynchronous document viewing module 190. The asynchronous document viewing module 190 allows a user that does not have the ability to access the system through the web interface described in the above paragraphs of this specification to securely view a copy of a document contained within the system.

In some embodiments, electronic copies of documents may be provided through a secure delivery system. The secure delivery system may be an embodiment of a document viewing module 190 or a separate system. A secure delivery system may be a system or module that allows an encrypted copy of a document to be sent to another computer and viewed by another authorized user. In some embodiments, the document viewing module 190 sends an initial email to a user and provides a link to download a digital certificate and software. The software can be installed on the user's computer. The system provides an option for a user of the system to use the secure delivery system to send an encrypted copy of any document to an authorized user of the secure delivery system. The document viewing module 190 then sends an email to the user of the secure delivery system that launches the software installed on the user's computer. The document viewing module 190 may provide an encrypted copy of the information that can be downloaded to the user's computer, so that the user of the secure delivery system can then view copies of the identified information. The encrypted copy of the information can only be decrypted for viewing with the software that the system provided in conjunction with the digital certificate provided by the system. The document remains encrypted whether stored on the user's computer or transmitted to another user.

In another embodiment, the document viewing module 190 delivers a "view only" certificate to a user. The certificate allows the user to view a copy of the information. In this embodiment, the document delivery module also sends an email to the user providing a link to the location of the copy of the information. The system then provides a viewable copy of the information accessible at the provided link.

The foregoing description of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

We claim:

1. A healthcare management system comprising:
   a storage unit; and
   a host computing device coupled to the storage unit, the host computing device configured to execute instructions including:
   receiving information from a plurality of healthcare providers,
   converting the received information from the plurality of healthcare providers into a common format;
   storing the converted information;
   providing access to the stored converted information, wherein access is allowed to at least two users of a plurality of users, the at least two users being members of different entities; and
   authorizing a user to access the stored converted information in a secure manner,
   wherein the host computing device is further configured to execute instructions including filtering out general healthcare information from occupational healthcare information.

2. The system of claim 1, wherein the host computing device is further configured to execute instructions including:
   receiving clinical data and billing data from the plurality of healthcare providers; and
   communicating with the plurality of healthcare providers in a secure manner.

3. The system of claim 1, wherein the host computing device is further configured to execute instructions including organizing the information into a logical workflow, wherein the logical workflow comprises a task for a user role to complete.

4. The system of claim 1, wherein the common format comprises a non-proprietary data format.

5. The system of claim 1, wherein the host computing device is further configured to execute instructions including organizing the information into injury cases.

6. The system of claim 1, wherein the host computing device is further configured to execute instructions including generating notifications based on the information received by the system.

7. The system of claim 1, wherein at least two of the plurality of users comprise a team.

8. The system of claim 1, wherein the host computing device is further configured to execute instructions including enabling a secure viewing of a copy of the information to a recipient by providing access to a secure webpage.

9. The system of claim 1, wherein the host computing device is further configured to execute instructions including delivering an encrypted copy of the information.

10. The system of claim 1, wherein the host computing device is further configured to execute instructions including allowing real-time communication among the plurality of users.

11. A method comprising:
    receiving, at a host computing device, information from a healthcare provider in a secure manner, the information comprising clinical data and billing data;
    storing, at a storage unit, the information from the healthcare provider;
    converting the information provided by the healthcare provider into a common format, at the host computing device;
    providing access, at the host computing device, to the information for a plurality of users wherein at least two of the plurality of users are members of different entities; and
    authorizing, at the host computing device, a user to access the information in a secure manner, wherein the authorizing occurs when the host computing device transmits a "view only" certificate to the user so that the user can view the information.

12. The method of claim 11, further comprising:
    receiving information from a plurality of healthcare providers; and
    communicating with the plurality of healthcare providers in a secure manner.

13. The method of claim 11, further comprising organizing the information into a logical workflow, wherein the organizing the information into the logical workflow comprises determining a task for a user role to complete.

14. The method of claim 13, wherein the common format comprises a non-proprietary data format.

15. The method of claim 11, further comprising organizing the information into injury cases.

16. The method of claim 13, further comprising generating notifications based on the information received by the system.

17. The method of claim 11, further comprising configuring at least two of the plurality of users into a team.

18. The method of claim 11, further comprising enabling a secure viewing of a copy of the information by a recipient by providing the recipient access to a secure webpage.

19. The method of claim 11, further comprising securely delivering a copy of the information by allowing the recipient to download an encrypted copy of the information to a desktop of the recipient.

20. The method of claim 11, further comprising filtering out general healthcare information from occupational healthcare information.

21. A method comprising:
    receiving, at a host computing device, information from a plurality of healthcare providers in a secure manner, the information comprising clinical data and billing data;
    filtering out general healthcare information from occupational healthcare information, at the host computing device;
    storing, at a storage unit, the information from the plurality of healthcare providers;
    providing access, at the host computing device, to the information for a plurality of users, wherein at least two of the plurality of users are members of different entities;
    authorizing, at the host computing device, a user to access the information in a secure manner, wherein the authorizing occurs when the host computing device transmits a "view only" certificate to the user so that the user can view the information;
    converting information provided by the plurality of healthcare providers into a non-proprietary data format, at the host computing device;
    organizing, at the host computing device, the information into injury cases; and
    organizing, at the host computing device, the information into a logical workflow, wherein the logical workflow comprises a task for a user role to complete.

22. The method of claim 21, wherein the non-proprietary data format comprises XML.

* * * * *